United States Patent [19]
Rosch et al.

[11] Patent Number: 6,009,558
[45] Date of Patent: Jan. 4, 2000

[54] ACTIVE WEAR GARMENTS

[75] Inventors: Paulette Mary Rosch, Sherwood; Donald Merlin Fries, deceased, late of Combined Locks, both of Wis., by Sharon Fries, administratrix

[73] Assignee: Kimberly-Clark Worldwide, Inc., Neenah, Wis.

[21] Appl. No.: 08/841,988

[22] Filed: Apr. 8, 1997

[51] Int. Cl.[7] .................................................. A41D 1/14
[52] U.S. Cl. ................................. 2/212; 2/80; 604/385.2
[58] Field of Search ............................. 2/70, 71, 72, 75, 2/80, 83, 79, 227, 212, 213, 243.1, 409; 604/385.1, 385.2

[56] References Cited

U.S. PATENT DOCUMENTS

| | | | |
|---|---|---|---|
| 2,526,978 | 10/1950 | Sullivan | 2/212 |
| 2,825,906 | 3/1958 | Stumpf | 2/212 |
| 2,827,638 | 3/1958 | Scharf | 2/212 |
| 2,835,897 | 5/1958 | Scruggs | 2/71 |
| 3,678,514 | 7/1972 | Safrit | 2/212 |
| 4,388,075 | 6/1983 | Mesek et al. | 604/385 |
| 4,606,964 | 8/1986 | Wideman | 428/152 |
| 4,639,949 | 2/1987 | Ales et al. | 2/400 |
| 4,657,802 | 4/1987 | Morman | 428/152 |
| 4,720,415 | 1/1988 | Vander Wielen et al. | 428/152 |
| 4,747,846 | 5/1988 | Boland et al. | 604/38 A |
| 4,798,603 | 1/1989 | Meyer et al. | 604/378 |
| 4,938,753 | 7/1990 | Van Gompel et al. | 604/385.2 |
| 4,938,754 | 7/1990 | Mesek | 604/385.2 |
| 4,938,757 | 7/1990 | Van Gompel et al. | 604/396 |
| 4,940,464 | 7/1990 | Van Gompel et al. | 604/396 |
| 5,114,781 | 5/1992 | Morman | 428/198 |
| 5,116,662 | 5/1992 | Morman | 428/198 |
| 5,204,997 | 4/1993 | Suzuki et al. | 2/400 |

FOREIGN PATENT DOCUMENTS 0 539 703 A1  5/1993  European Pat. Off. ........ A61F 13/15

*Primary Examiner*—John J. Calvert
*Assistant Examiner*—Kate Moran
*Attorney, Agent, or Firm*—Patricia A. Charlier

[57] ABSTRACT

The process friendly garments include a waste containment structure that has an absorbent core which is positioned between a wearer and a backsheet, and a cover joined to the pant structure.

6 Claims, 5 Drawing Sheets

ACTIVE WEAR GARMENTS

BACKGROUND OF THE INVENTION

This invention pertains to a process friendly disposable garment, and more particularly to a disposable garment that may be adapted to provide containment and absorbency of waste matter while being useful as active and swim wear.

Currently, disposable waste containment garments find widespread use in the areas of adult care, infant care, and child care, and have generally replaced reusable cloth garments. Disposable diapers, for example, have met a particular need and have become very popular. Disposable training pants have also met a particular need and have become popular. A problem exists with the design of active and swim wear. Neither active or swim wear is designed to accommodate a waste containment structure. Further, the design of the current active and swim wear does not keep waste containment structures in place during swimming and other activities.

SUMMARY OF THE INVENTION

Thus, there is a need to provide an improved active and swim wear that minimizes the leakage of urine and fecal matter during a variety of activities including play, swimming, and travel to swimming while maintaining fecal containment during the activities. In response to this need, improved shorts and pant garments have been discovered.

A waste containment garment according to the invention includes a waste containment structure having a longitudinal axis and opposite longitudinally spaced ends and a cover defining opposite waist regions. The waste containment structure comprises an absorbent core, a backsheet and an elastic member located in the waist regions to hold the structure in place. The elastic members are operatively joined to the cover. However, the waste containment structure can remain snugly in place while resisting movement in response to the cover.

The present invention relates to a disposable garment comprising a skirt cover having a front panel having two side edges and a waist region and an opposing bottom edge between the side edges and a back panel having two side edges and a waist region and an opposing bottom edge between the side edges. The garment also includes a pant structure having a front waist band region and a back waist band region longitudinally spaced and terminating in longitudinal ends, a crotch area between the front and back waist band regions, and a pair of side panels. The pant structure includes a waist opening, two leg openings and waist elastic members, wherein the waist region of the front panel and the waist region of the back panel of the skirt cover are non-refastenably engaged to the front waist band region and the back waist band region having the waist elastic members positioned between the panels and the waist band regions.

In another aspect of the invention, a three-dimensional waste containment garment includes a waste containment structure and a cover. The full cover has an outer surface and an opposing inner surface and defines at least a waist opening. The cover is joined to the waste containment structure at least at a portion of the waist opening. A waste containment structure of the garment has a longitudinal axis, opposite longitudinally spaced ends, and side edges extending between the ends. The waste containment structure includes a liquid permeable liner, a backsheet attached to the liner, and an absorbent core sandwiched between the liner and backsheet. The cover is elastically connected to the ends of the waste containment structure.

Numerous features and advantages of the present invention will appear from the following description. In the description, reference is made to the accompanying drawings which illustrate desired embodiments of the invention. Such embodiments do not represent the full scope of the invention. Reference should, therefore, be made to the claims herein for interpreting the full scope of the invention.

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings, wherein.

DEFINITIONS

Figure 1:
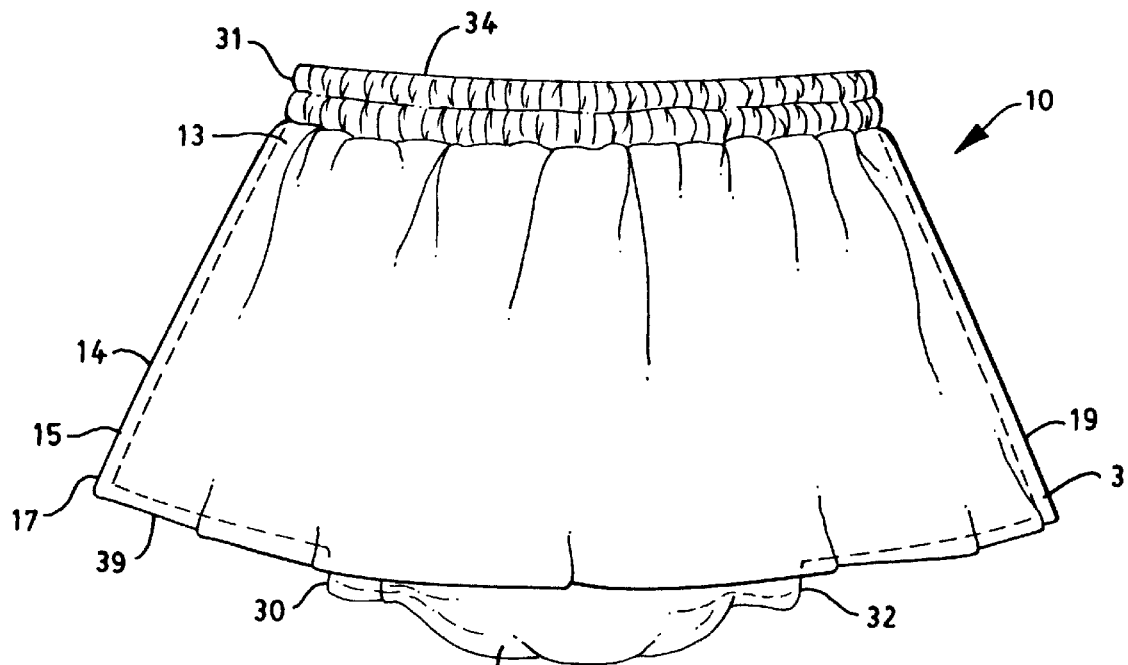
FIG. 1 is a front view of a skirt cover and pant structure typifying an embodiment of the present invention.

Within the context of this specification, each term or phrase below will include the following meaning or meanings:

(a) "Bonded" refers to the joining, adhering, connecting, attaching, or the like, of two elements. Two elements will be considered to be bonded together when they are bonded directly to one another or indirectly to one another, such as when each is directly bonded to intermediate elements.

(b) "Disposable" includes being disposed of after use, and not intended to be washed and reused.

(c) "Disposed", "disposed on", "disposed with", "disposed at", "disposed near", and variations thereof are intended to mean that one element can be integral or unitary with another element, or that one element can be a separate structure joined to or connected to or placed with or placed near another element.

(d) "Elasticity" and "elastic" include that property of a material by virtue of which it tends to substantially recover to its original size and shape after removal of a force causing deformation of the material.

(e) "Elastically connected" and "elastically connecting" refer to two elements being separated by and bonded to an elastic member, where the relative position of the two elements may change due to extension of the elastic member.

(f) "Elongation" includes the ratio of the extension of a material to the length of a material prior to the extension. Elongation is expressed in percent.

(g) "Extension", "extend", and "extended" include the change in length of a material due to stretching. Extension is expressed in units of length.

(h) "Force" includes a physical influence exerted by one body on another which produces acceleration of bodies that are free to move and deformation of bodies that are not free to move. Force is expressed in grams-force.

(i) "Foreshortened" and "foreshortening" include to shorten beforehand, that is, before a subsequent step.

(j) "Front" and "back" are used to designate relationships relative to the garment itself, rather than to suggest any position the garment assumes when it is positioned on a wearer.

(k) "Member" when used in the singular can have the dual meaning of a single element or a plurality of elements.

(l) "Operatively joined" with reference to the attachment of an elastic member to another element means that the elastic member when attached to or connected to or treated with heat with the element gives that element elastic properties. With reference to the attachment of a non-elastic member to another element, it means that the member and element can be attached in any suitable manner that permits or allows them to perform the intended or described function of the joinder. The joining, attaching, connecting or the like can be either directly, such as joining either member directly to an element, or can be indirectly by means of another member or element disposed between the first member and the first element.

(m) "Pervious" means that a layer of material is able to pass or transport a detectable amount of liquid under conditions normally encountered in a diaper/pant during use.

(n) "Porous" means that a layer of material is able to pass or transport a measurable amount of liquid under conditions normally encountered in a diaper/pant during use.

(o) "Rupture" includes the breaking or tearing apart of a material; in tensile testing, rupture refers to the total separation of a material into two parts either all at once or in stages, or the development of a hole in some materials.

(p) "Stretch bonded" refers to an elastomeric strand being bonded to another member while the elastomeric strand is elongated at least about 25 percent of its relaxed length. Desirably, the term "stretch bonded" refers to the situation wherein the elastomeric strand is elongated at least about 100 percent, more desirably at least about 300 percent, of its relaxed length when it is bonded to the other member.

(q) "Stretch bonded laminate" ("SBL") refers to a composite material having at least two layers in which one layer is a gatherable layer and the other layer is a stretchable, that is, elastic, layer. The layers are joined together when the stretchable layer is in a stretched condition so that upon relaxing the layers, the gatherable layer is gathered.

(r) "Tension" includes a uni-axial force tending to cause the extension of a body or the balancing force within that body resisting the extension.

(s) "Two-dimensional" refers to a garment, such as a diaper, that can be opened and laid in a flat condition without destructively tearing any structure. This type of garment does not have continuous leg and waist openings when opened and laid flat, and requires a fastening device, such as adhesive tapes, to attach the garment about the wearer.

(t) "Three-dimensional" refers to a finished garment similar to shorts or pants in that they have continuous leg and waist openings that are bounded by the material of which the garment is made. This type of garment can be opened and laid flat only by destructively tearing it. This type of garment may or may not have manually tearable seams.

(u) "Ultimate elongation" includes the elongation at the point of rupture.

These definitions are not intended to be limiting and these terms may be defined with additional language in the remaining portion of the specification.

DESCRIPTION OF A DESIRED EMBODIMENT

Figure 2:
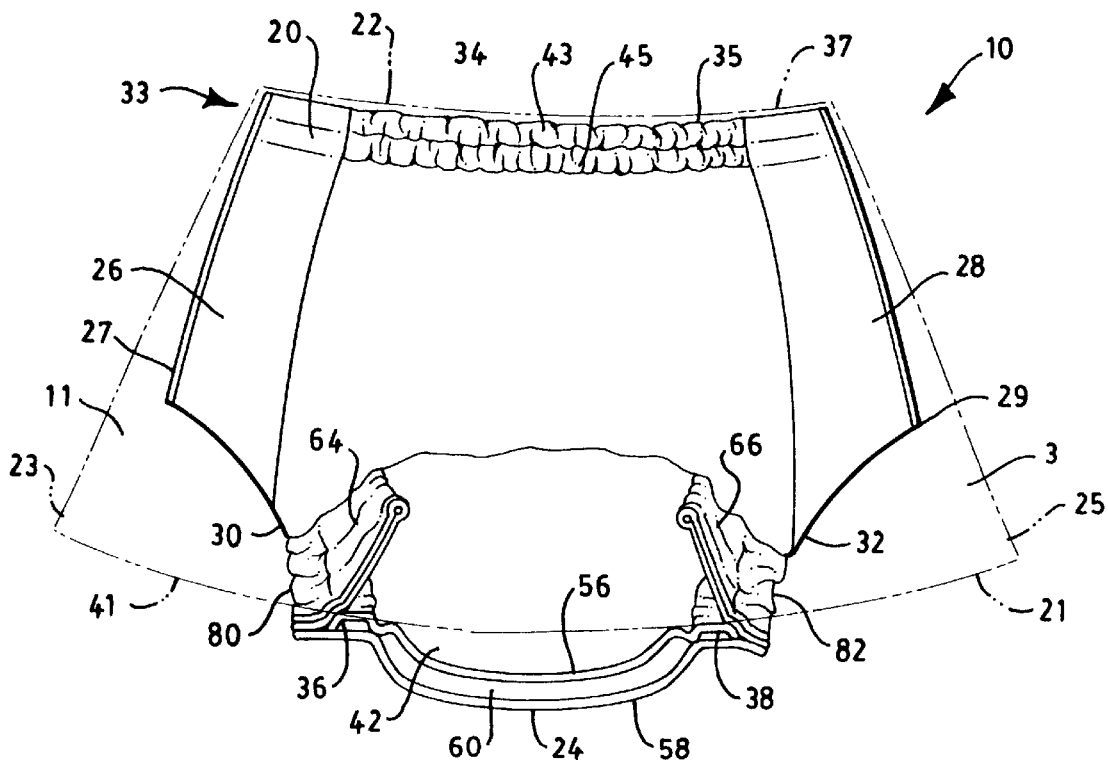
FIG. 2 is a front cut away view of a skirt cover and pant structure typifying an embodiment of the present invention.

A garment 10, a pant and skirt combination, of the present invention, as shown in FIGS. 1 and 2, includes a pant structure 12 and a skirt cover 14. The garment 10 is intended to resemble swimwear or outer active wear clothing. At the same time, the garment 10 may be constructed such that the skirt cover 14 remains securely in place about the wearer's waist with the pant structure 12 including a waste containment structure 42 positioned to receive and contain voided material. The garment 10 can be made or constructed in a variety of ways, one of which is described in U.S. Pat. application Ser. No. 043,132 filed on Mar. 25, 1993, which is incorporated by reference herein. Other pant designs are described in U.S. Pat. Nos. 4,938,757, 4,747,846, and 4,940, 464; the contents of these three patents are incorporated by reference herein.

The skirt cover 14 includes opposing inner surface 11 and outer surface 13. The skirt cover 14 is made up of a front panel 15 and a back panel 21. The front panel 15 has a pair of side edges 17 and 19 and opposing waist region 31 and bottom edge 39 positioned between the side edges 17 and 19. The back panel 21 has a pair of side edges 23 and 25 and opposing waist region 33 and bottom edge 41 positioned between the side edges 23 and 25. The front panel 15 and the back panel 21 may or may not extend to form an overlapping configuration at the sides of the garment 10.

In the desired embodiment of the present invention, the side edges 17, 19, 23, and 25 are not joined or fastened together, forming a two-pieced skirt cover 14. In another embodiment of the present invention, the side edge 17 is joined or fastened to the side edge 23 at the side seam 87 and the side edge 19 is joined or fastened to the side edge 25 at the side seam 89, forming a one piece skirt cover 14.

The side edges 17, 19, 23, and 25 and the bottom edges 39 and 41 can be hemmed. For easier manufacture, the side edges 17, 19, 23, and 25 and the bottom edges 39 and 41 are left unhemmed, facilitating easy machine cutoff.

In some embodiments of the present invention, the side seams 87 and 89 are non-refastenable. Non-refastenable seams 87 and 89 may be formed by any suitable means such as ultrasonic sealing, adhesive bonding, heat sealing, or the like. One suitable methods of forming such seams is disclosed in U.S. Pat. No. 4,938,753 issued Jul. 3, 1990, to Van Gompel et al., which is incorporated herein by reference. As illustrated most clearly in FIG. 2, the non-refastenable seams 27 and 29 of side panels 26 and 28 may be bonded together to form manually tearable, non-refastenable seams. The pant structure 12 thus defines a waist opening 34 and a pair of leg openings 30 and 32 (FIGS. 1 and 2).

In other embodiments of the present invention, the side seams 87 and 89 are refastenable. Refastenable means for securing the side edges 17, 19, 23, and 25 include adhesives and mechanical type fasteners 96. Mechanical type fasteners include buttons, button holes, snaps, buckles, clasps, hooks and loops, end extensions, tabs, and the like which are designed or adapted to interlock or engage some type of a complimentary device or the inner surface 11 or outer surface 13 of the skirt cover 14. In addition, elasticized fasteners may also be used in assuring better fit of the garment 10.

Figure 3:
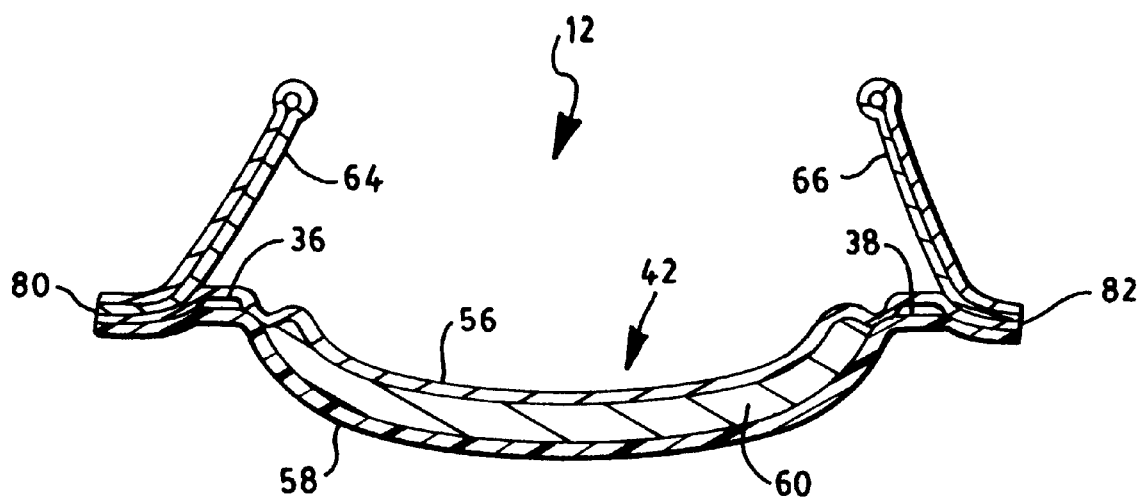
FIG. 3 is a cross sectional view of the waste containment structure.

The pant structure 12 (See FIG. 3) includes a front and back longitudinally spaced waist band regions 20 and 22, which terminate in longitudinal ends 35 and 37 of the pant structure 12. A crotch area 24 is located between the front waist band region 20 and the back band waist region 22. The left side panel 26 and the right side panel 28 extend between the front waist region 20 and the back waist region 22. The pant structure 12 may include a waste containment section 42. The waste containment structure 42 may include a backsheet 58, a bodyside liner 56, an absorbent core 60 as well as the side panels 26 and 28. In some embodiments, containment flaps 64 and 66 are included in the waste containment structure 42.

Side panels 26 and 28, which may or may not have elastic elements, are ultrasonically bonded and are formed such that the materials of construction provide a manually tearable, non-refastenable region near the seams 27 and 29. The side panels 26 and 28 can incorporate elastic elements which include incorporating a layer of elastic material or an SBL.

The pant structure 12 also desirably includes leg elastics 36 and 38 operatively joined to the crotch area 24. The leg elastics 36 and 38 are positioned along the edges of side panels 26 and 28 and the longitudinal edges 80 and 82 of the pant structure 12 or the waste containment structure 42 in the crotch area 24. The leg elastics 36 and 38 may assist in holding the pant structure 12, and ultimately the waste containment structure 42 where present, against the body of the wearer or forming seals or gaskets about the legs of the wearer.

Leg elastics 36 and 38 can be stretch bonded to the cover material along the longitudinal edges of the pant structure 12. The waist elastic 43 and 45 elasticizes the front and back waist band regions 20 and 22 of the pant structure 12. Thereafter, each side panel 26 and 28 can be bonded together by seams 27 and 29 so that the pant structure 12 defines the waist opening 34 and the pair of leg openings 30 and 32.

The pant structure 12 and the skirt cover 14 are joined at the waist of the garment 10. The longitudinal ends 35 and 37 of the waist band regions 20 and 22 of the pant structure 12 are joined to the waist regions 31 and 33. Waist elastic members 43 and 45 are positioned between the longitudinal ends 35 and 37 and the waist regions 31 and 33.

The waist elastic members 43 and 45 may be stretch bonded to the waist regions 31 and 33 of the skirt cover 14 and the waist band regions 20 and 22 of the pant structure 12 or bonded in a relaxed state to a gathered portion of the waist band regions 20 and 22 of the pant structure 12 and the waist regions 31 and 33 of the skirt cover 14. One suitable method for attaching the waist elastics 43 and 45 is disclosed in U.S. Pat. No. 4,639,949 issued Feb. 7, 1987, to Ales et al., which is incorporated herein by reference.

Desirably, the waist elastic members 43 and 45 are made up of at least two spunbond layers with elastic positioned between the spunbond layers. The longitudinal ends 35 and 37, waist regions 31 and 33, and the waist elastic members 43 and 45 are desirably bonded together by adhesives, however other methods of bonding discussed above can be utilized. The waist regions 31 and 33 of the skirt cover 14 may be attached to the pant structure 12 around the entirety of the waist opening 34 or only a portion thereof.

The longitudinal ends 35 and 37 and the waist regions 31 and 33 end at the top edge or near the top edge of the waist elastic members 43 and 45. This allows the longitudinal ends 35 and 37 and the waist regions 31 and 33 to be cut off simultaneously.

The garment 10 may include a waste containment structure 42. With reference to FIG. 2, the waste containment structure 42 as illustrated includes a backsheet 58, a substantially liquid permeable bodyside liner 56, and an absorbent core 60 sandwiched between the backsheet 58 and the bodyside liner 56. The backsheet 58 and bodyside liner 56 are desirably longer and wider than the absorbent core 60, so that the peripheries of the backsheet 58 and liner 56 form margins which may be sealed together using ultrasonic bonds, thermal bonds, adhesives, or other suitable means. The absorbent core 60 may be attached to the backsheet 58 and/or the bodyside liner 56 using ultrasonic bonds, adhesives, or other suitable means.

The waste containment structure 42 may also include additional components to assist in the acquisition, distribution and storage of waste material. For example, the waste containment structure 42 may include a transport layer, such as described in U.S. Pat. No. 4,798,603 issued Jan. 17, 1989, to Meyer et al., or a surge management layer, such as described in European Patent Application EP 0 539 703 A1, published May 5, 1993, which patent and application are incorporated herein by reference.

The waste containment structure 42 can be constructed by supplying bodyside liner and backsheet materials and sandwiching an individual absorbent core 60 between the backsheet 58 and bodyside liner 56. The side peripheries of the backsheet 58 and bodyside liner 56 outward of the absorbent core 60 can be joined with side panel material and sealed together. Individual waste containment structure 42 can then be cut from the continuous supply of backsheet and bodyside liner materials. The waste containment structure 42 may optionally be T-shaped, I-shaped, hourglass-shaped, or irregularly-shaped.

The absorbent core 60 can comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers. Absorbent core 60 can comprise only coform, or a combination of superabsorbent materials and coform, with other absorbent or non-absorbent materials.

The coform material may comprise an airlaid blend of cellulosic wood fibers and meltblown polyolefin fibers, such as polyethylene or polypropylene fibers, or may comprise an air-formed batt of cellulosic fibers (i.e., wood pulp fluff). Optionally, the absorbent core 60 may be treated with a surfactant to aid in liquid acquisition when in a dry environment. In particular embodiments of the invention, the absorbent core 60 has a bulk thickness of not more than about 1.25 cm when dry. The hydrophilic fibers and polymer strands may be provided in a fiber-to-polymer ratio which is less than 80:20, for example between about 30:70 and about 80:20 and, desirably between about 60:40 and about 70:30.

For absorbent core 60, compounds to increase the core absorbency, are included in an effective amount and may consist of organic or inorganic high-absorbency materials. For example, the absorbent core 60 can include 0–5 weight percent high-absorbency material, desirably less than 1%. Suitable inorganic high-absorbency materials include, for example, absorbent clays and silica gels.

Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine or the like. Other suitable polymers can include hydrolyzed acrylonitrile grafted starch, acrylic acid grafted starch, and isobutylene maleic anhydride copolymers, and mixtures thereof.

The hydrogel polymers are desirably sufficiently cross-linked to render the materials substantially water-insoluble. Cross-linking may, for example, be by irradiation or by covalent, ionic, van der Waals or hydrogen bonding. Suitable materials are available from various commercial vendors, such as Dow Chemical Company, Hoechst-Celanese Corporation and Allied-Colloid. Typically, the high-absorbency material is capable of absorbing at least about 15 times its weight in water, and desirably is capable of absorbing more than about 25 times its weight in water.

The high-absorbency material can be distributed or otherwise incorporated into the absorbent core 60 employing various techniques. For example, the high-absorbency material can be substantially uniformly distributed among the fibers comprising the absorbent core 60. The materials can also be non-uniformly distributed within the absorbent core 60 fibers to form a generally continuous gradient with either an increasing or decreasing concentration of high-absorbency material, as determined by observing the concentration moving inward from the backsheet 58. Alternatively, the high-absorbency material can comprise a discrete layer separate from the fibrous material of the absorbent core 60, or can comprise a discrete layer integral with the absorbent core 60.

The absorbent core 60 may also include a wrap layer (not shown) to help maintain the integrity of the fibrous core. This wrap may comprise a hydrophilic spunbond, meltblown or bonded-carded web material composed of synthetic polymer filaments, such as polypropylene, polyethylene, polyesters or the like or natural polymer filaments such as rayon or cotton.

The waste containment structure 42 most desirably incorporates a backsheet 58 which is vapor pervious and liquid pervious but only to a small degree liquid pervious. It is desirably associated with a cover structure (not shown) which is liquid impervious and which covers or separates the inner waste containment structure from contact with outside surfaces or people.

The crotch area 24 of the waste containment structure 42 could be rendered liquid-impervious by appropriate means such as plastic film, while the upper portion and the waist opening 34 of the waste containment structure 42 could be covered by a liquid-pervious material, to aid in breathability.

The backsheet 58 may comprise a thin, liquid impermeable web or sheet of plastic film such as polyethylene, polypropylene, polyvinyl chloride or similar material. Alternately, the backsheet 58 may comprise a nonwoven, fibrous web which has been suitably constructed and arranged to have low liquid perviousness. Still alternately, the backsheet 58 may comprise a layered or laminated material, such as a thermally bonded plastic film and nonwoven web composite. Since the garment 10 is typically intended for active wear, an exposed backsheet or portions thereof, can be made of materials or of a basis weight which is abrasion resistant.

The backsheet 58 may be constructed of a single spunbonded polypropylene nonwoven web having a basis weight of about 0.5 oz/yd$^2$ (17 gsm) to about 2.0 oz/yd$^2$ (68 gsm). The skirt cover 14 desirably comprises a material having a basis weight of from about 0.5 oz/yd$^2$ (17 gsm) to about 2.0 oz/yd$^2$ (68 gsm), desirably 1.0 oz./yd$^2$ to 2.0 oz./yd$^2$ at least in the crotch and buttocks regions of the backsheet 58. Lesser basis weights may be used in other regions of the garment 10.

In the waste containment structure 42, the backsheet 58 can also be liquid-pervious, and the cover liquid-impervious, for the same reasons as above. However, wherein the garment 10 has a skirt cover 14, the crotch area 24 of the waste containment structure 42 could be rendered liquid-impervious by appropriate means such as a plastic film, while the upper portion of the waste containment structure 42 could be covered by a liquid-pervious material, to aid in breathability.

The bodyside liner 56 may be any soft, flexible, porous sheet which passes fluids therethrough. Again, the bodyside liner 56 must permit submersion in fresh water, salt water, or treated water and still retain its integrity. The bodyside liner 56 may comprise, for example, a nonwoven web or sheet of a spunbonded, meltblown or bonded-carded web composed of synthetic polymer filaments, such as polypropylene, polyethylene, polyesters or the like, or a web of natural polymer filaments such as rayon or cotton. The bodyside liner 56 has a pore size that readily allows the passage therethrough of liquids, such as urine and other body exudates. The bodyside liner 56 may be selectively embossed or perforated with discrete slits or holes extending therethrough. Suitable adhesives for adhering the laminate layers can be obtained from Findley Adhesives, Inc. of Wauwatosa, Wis.

As described previously, the side panels 26 and 28 may be formed of a material capable of stretching in one direction or capable of stretching in at least two substantially perpendicular directions. One suitable one-directional stretch material is disclosed in U.S. Pat. No. 4,720,415 issued Jan. 19, 1988, to Vander Wielen et al., which is incorporated herein by reference. The one-directional stretch material may comprise a composite material including at least one gatherable web bonded to at least one elongated elastic web.

The elastic web may be an elastic film or nonwoven fibrous elastic webs such as meltblown elastomeric fibrous webs. In one embodiment, the side panels 26 and 28 comprise a stretch bonded laminate formed of a pre-stretched elastic meltblown inner layer sandwiched between and attached to a pair of spunbond polypropylene nonwoven webs having a basis weight of about 0.4 oz/yd$^2$ (13.6 gsm). Suitable elastic materials can be purchased from the Shell Chemical Company of Houston, Tex. under the trade name Kraton. Other suitable one-directional stretch materials are disclosed in U.S. Pat. No. 4,606,964 issued Aug. 19, 1986, to Wideman and U.S. Pat. No. 4,657,802 issued Apr. 14, 1987, to Morman.

The material that can be used for the elastic element which can be used for the side panels 26 and 28 desirably has stretch characteristic in the first direction such that it is capable of from about 10 to about 500 percent elongation and upon release of tension will recover at least 55 percent of its elongation. It is generally desired that the material for use in the side panels 26 and 28 in the first direction be capable of between about 50 and about 300 percent elongation, particularly at least 125 percent elongation and recovery upon release of tension of at least 80 percent of its elongation.

Suitable two-directional stretch materials for the side panels 26 and 28 are disclosed in U.S. Pat. No. 5,114,781 issued May 19, 1992, and U.S. Pat. No. 5,116,662 issued May 26, 1992, to Morman, which are incorporated herein by reference. A two-directional stretch material may comprise a composite material including a neckable material and an elastic sheet, which may be formed by meltblowing or extrusion. Neckable materials are those which may be constricted in at least one dimension by applying a tensioning force in a direction perpendicular to the desired direction of neck-down, and may include a spunbonded, meltblown or bonded carded web.

The tensioned, necked neckable material may be joined to the elongated elastic sheet at spaced locations arranged in a nonlinear configuration. Another two-directional stretch composite material may comprise one or more layers of reversibly necked material joined to one or more layers of elastic sheet at spaced locations. Reversibly necked materials are those that have been treated, such as with heat, while necked to impart memory to the material so that, when a force is applied to extend the material to its pre-necked dimensions, the treated, necked portions will generally recover to their necked dimensions upon termination of the force.

The leg elastics 36 and 38 and waist elastic members 43 and 45 may be formed of a stretch bonded laminate. In particular, the stretch bonded laminate may comprise at least one nonwoven gatherable layer and an elastic layer. Alternately, the leg elastics 36 and 38 and waist elastic 43 and 45 may be formed of a dry-spun coalesced multifilament elastomeric thread sold under the tradename LYCRA and available from I.E. Du Pont de Nemours and Company. Still alternately, the leg elastics 36 and 38 and waist elastic members 43 and 45 may be formed of other typical elastics utilized in the diaper-making art, such as a thin ribbon of elastic material as disclosed in U.S. Pat. No. 4,940,464 issued Jul. 10, 1990, to Van Gompel et al., which is incorporated herein by reference. Elasticity could also be imparted to the longitudinal side sections by extruding a hot melt elastomeric adhesive between the backsheet 58 and the bodyside liner 56. Other suitable elastic gathering means are disclosed in U.S. Pat. No. 4,938,754 to Mesek and U.S. Pat. No. 4,388,075 to Mesek et al.

The skirt cover 14 can be desirably constructed of a single layer comprising film layer, nonwoven layer, or any other suitable liquid permeable or liquid impermeable material, desirably having a cloth-like feel. The skirt cover 14 is constructed of a single spunbonded polypropylene nonwoven web having a basis weight of about 0.5 oz/yd$^2$ (17 gsm) to about 2.0 oz/yd$^2$ (68 gsm).

The skirt cover 14 typically comprises a material having a basis weight of from about 0.5 oz/yd$^2$ (23.8 gsm) to about 2.0 oz/yd$^2$ (68 gsm). The skirt cover 14 may comprise a second layer of a liquid impermeable film layer suitably joined to the first layer by adhesive. The first layer of the skirt cover 14 may be spunbonded polypropylene nonwoven web having a basis weight of from about 0.5 oz/yd$^2$ (23.8 gsm) to about 2.0 oz/yd$^2$ (68 gsm). The second layer of the skirt cover 14 may be a polyethylene film ranging from about 0.5 to about 1.0 mil in thickness.

Figure 4:
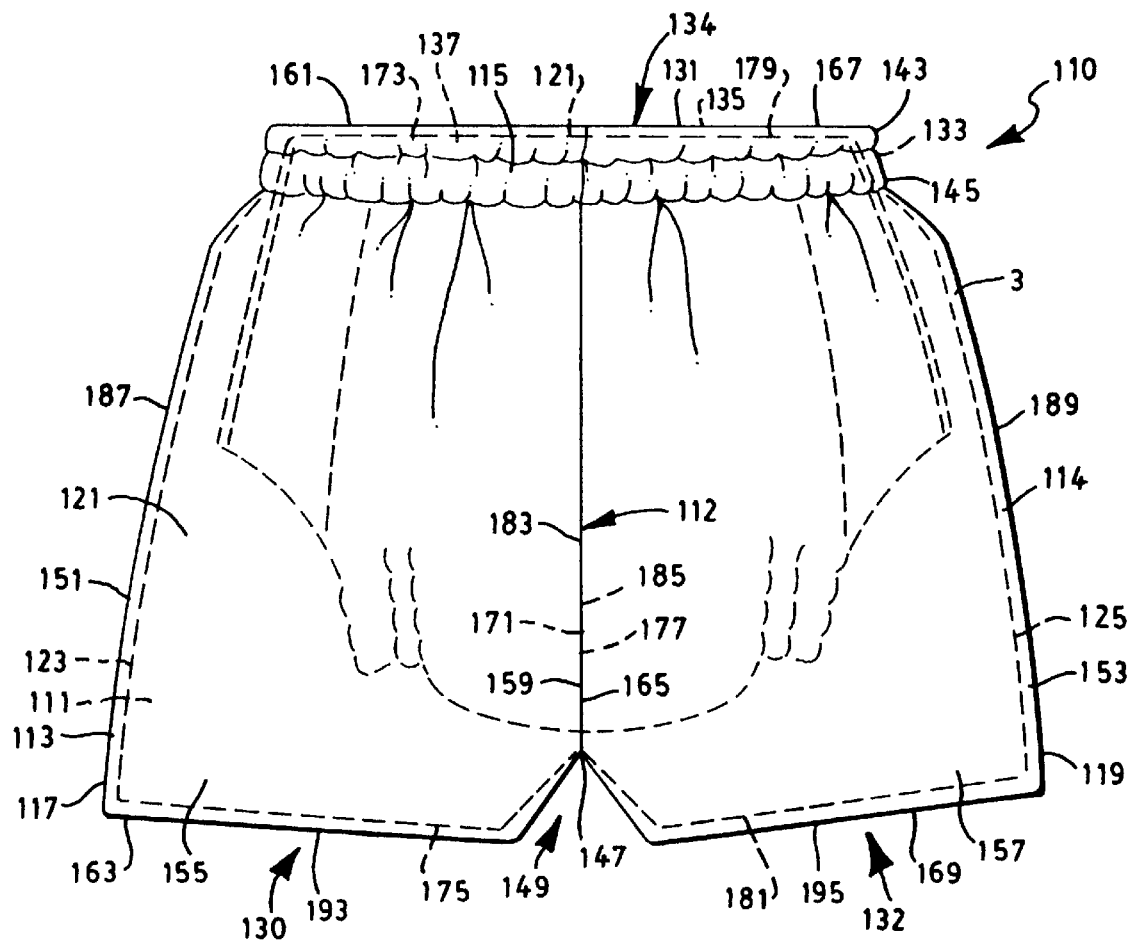
FIG. 4 is a front view of a trunk cover and pant structure typifying an embodiment of the present invention.

The trunk garment 110 is illustrated in FIG. 4. The trunk cover 114 includes opposing inner and outer surfaces 111 and 113. According to the desired embodiment, the trunk cover 114 of the trunk garment 110 desirably comprises a right front panel 151, a left front panel 153, a right back panel 155, and a left back panel 157. The right front panel 151 has a pair of side edges 117 and 159 and opposing waist region 161 and bottom edge 163 positioned between the side edges 117 and 159. The left front panel 153 has a pair of side edges 119 and 165 and opposing waist region 167 and bottom edge 169 positioned between the side edges 119 and 165.

The right back panel 155 has a pair of side edges 123 and 171 and opposing waist region 173 and bottom edge 175 positioned between the side edges 123 and 171. The left back panel 157 has a pair of side edges 125 and 177 and opposing waist region 179 and bottom edge 181 positioned between the side edges 125 and 177.

The side edge 159 is joined to the side edge 165 at the center seam 183 forming a front waist region 131 and a front panel 115. The side edge 171 is joined to the side edge 177 at the center seam 185 forming a back waist region 133 and a back panel 121. The side edge 117 is joined to the side edge 123 at the side seam 187 and the side edge 119 is joined to the side edge 125 at the side seam 189.

The front panel 115 and the back panel 121 of the trunk cover 114 are joined together at the inseam 147 so as to define a crotch section 149 extending centrally between the front and back panels 115 and 121 respectively. The front panel 115, the back panel 121, and the crotch section 149 when joined together define a waist opening 134, and two leg openings 187 and 189 at opposite sides of the crotch section 149.

In the embodiments of the trunk garment 110 where a pant structure 112 is not included, the waist regions 131 and 133 joined to waist elastic members 143 and 145 on the inner surface 111 of the trunk cover 114. Although not as desirable, the waist elastic members 143 and 145 could be joined to the outer surface 113 of the trunk cover 114.

The waist elastic members 143 and 145 may be stretch bonded to the waist regions 131 and 133 of the trunk cover 114 or bonded in a relaxed state to a gathered portion the waist regions 131 and 133 of the trunk cover 114. One suitable method for attaching the waist elastics 143 and 145 is disclosed in U.S. Pat. No. 4,639,949 issued Feb. 7, 1987, to Ales et al., which is incorporated herein by reference.

Desirably, the waist elastic members 143 and 145 are made up of at least two spunbond layers with elastic positioned between the spunbond layers. The waist regions 131 and 133 and the waist elastic members 143 and 145 are desirably bonded together by adhesives, however other methods of bonding discussed above can be utilized. The waist regions 131 and 133 of the trunk cover 114 may be attached to the waist elastic members 143 and 145 around the entirety of the waist opening 134 or only a portion thereof.

The waist regions 131 and 133 end at the top edge or near the top edge of the waist elastic members 143 and 145. This allows the waist regions 131 and 133 to be cut off simultaneously. The bottom edges 163, 169, 175, and 181 can be hemmed. For easier manufacture, the bottom edges 163, 169, 175, and 181 are left unhemmed, facilitating easy machine cutoff.

According to another embodiment of the present invention, see FIGS. _, the trunk cover 114 of the trunk garment 110 desirably comprises a front panel 115 and a back panel 121. The front panel 115 has a pair of side edges 117 and 119 and opposing waist region 131 and bottom edge 139 positioned between the side edges 117 and 119. The back panel 121 has a pair of side edges 123 and 125 and opposing waist region 133 and bottom edge 141 positioned between the side edges 123 and 125. The side edge 117 is joined to the side edge 123 at the side seam 187 and the side edge 119 is joined to the side edge 125 at the side seam 189.

Figure 5:
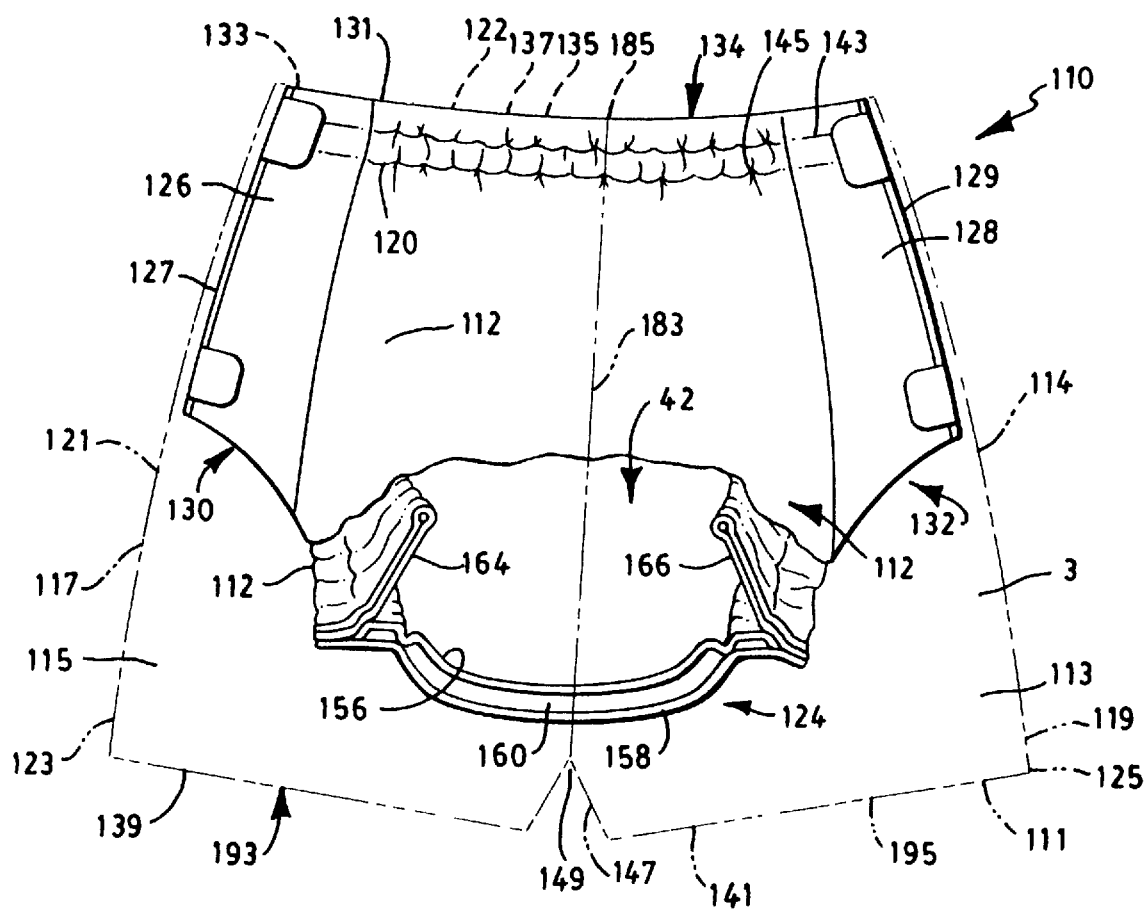
FIG. 5 is a front cut away view of a trunk cover typifying an embodiment of the present invention.

In some embodiments of the present invention, the side seams 187 and 189 are non-refastenable. Non-refastenable seams 187 and 189 may be formed by any suitable means such as ultrasonic sealing, adhesive bonding, heat sealing, or the like. One suitable methods of forming such seams is disclosed in U.S. Pat. No. 4,938,753 issued Jul. 3, 1990, to Van Gompel et al., which is incorporated herein by reference. As illustrated most clearly in FIG. 5, the non-refastenable seams 127 and 129 of side panels 126 and 128 may be bonded together to form manually tearable, non-refastenable seams. The pant structure 112 thus defines a waist opening 134 and a pair of leg openings 130 and 132 (FIGS. 1 and 2).

In other embodiments of the present invention, the side seams 187 and 189 are refastenable. Refastenable means for securing the side edges 117, 119, 123, and 125 include adhesives and mechanical type fasteners 96 Mechanical type fasteners include buttons, button holes, snaps, buckles, clasps, hooks and loops, end extensions, tabs, and the like which are designed or adapted to interlock or engage some type of a complimentary device or the inner surface 111 or outer surface 113 of the skirt cover 114. In addition, elasticized fasteners may also be used in assuring better fit of the garment 110.

The front panel 115 and the back panel 121 of the trunk cover 114 are joined together at the inseam 147 so as to define a crotch section 149 extending centrally between the front and back panels 115 and 121 respectively. The front panel 115, the back panel 121, and the crotch section 149 when joined together define a waist opening 134, and two leg openings 193 and 195 at opposite sides of the crotch section 149.

In the embodiments of the trunk garment 110 where a pant structure 112 is not included, the waist regions 131 and 133 joined to waist elastic members 143 and 145 on the inner surface 111 of the trunk cover 114. Although not as desirable, the waist elastic members 143 and 145 could be joined to the outer surface 113 of the trunk cover 114.

The waist elastic members 143 and 145 may be stretch bonded to the waist regions 131 and 133 of the trunk cover 114 or bonded in a relaxed state to a gathered portion the waist regions 131 and 133 of the trunk cover 114. One suitable method for attaching the waist elastics 143 and 145 is disclosed in U.S. Pat. No. 4,639,949 issued Feb. 7, 1987, to Ales et al., which is incorporated herein by reference.

Desirably, the waist elastic members 143 and 145 are made up of at least two spunbond layers with elastic positioned between the spunbond layers. The waist regions 131 and 133 and the waist elastic members 143 and 145 are desirably bonded together by adhesives, however other methods of bonding discussed above can be utilized. The waist regions 131 and 133 of the trunk cover 114 may be attached to the waist elastic members 143 and 145 around the entirety of the waist opening 134 or only a portion thereof.

The waist regions 131 and 133 end at the top edge or near the top edge of the waist elastic members 143 and 145. This allows the waist regions 131 and 133 to be cut off simultaneously. The bottom edges 139 and 141 can be hemmed. For easier manufacture, the bottom edges 139 and 141 are left unhemmed, facilitating easy machine cutoff.

The trunk garment 110 can be formed in a continuous process by supplying a cover material including individual portions that define a single cover having waist regions 131 and 133 and front and back panels 115 and 121 extending from the waist regions 131 and 133. The crotch section 149 is formed between the front and back panels 115 and 121. The panels 115 and 121 can be shaped by die cutters, water jet cutters or other suitable means.

Figure 6:
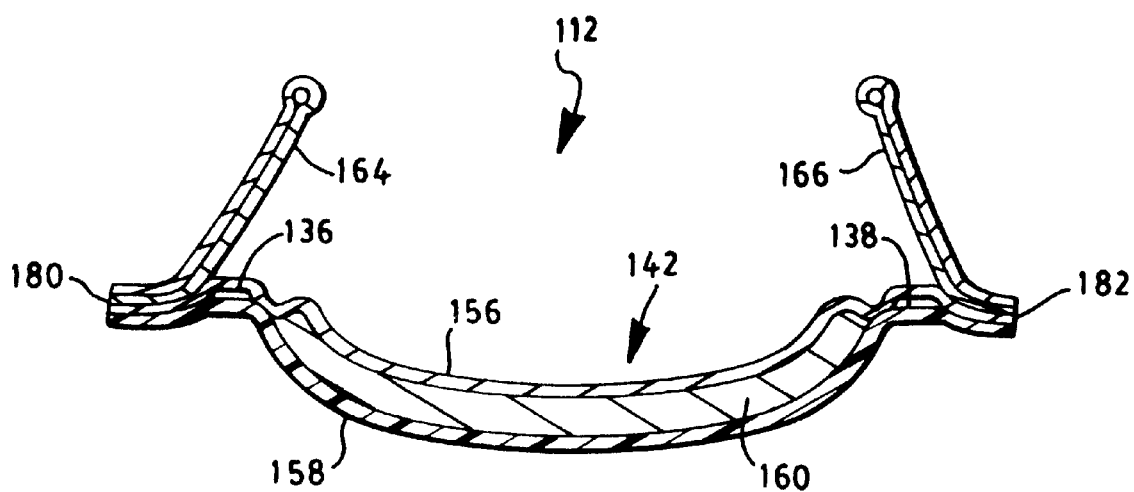
FIG. 6 is a cross-sectional view of the waste containment structure.

The pant structure 112 (See FIG. 5 and 6) includes a front and back longitudinally spaced waist band regions 120 and 122, which terminate in longitudinal ends 135 and 137 of the pant structure 112. A crotch area 124 is located between the front waist band region 120 and the back band waist region 122. The left side panel 126 and the right side panel 128 extend between the front waist region 120 and the back waist region 122. The pant structure 112 may include a waste containment section 142. The waste containment structure 142 may include a backsheet 158, a bodyside liner 156, an absorbent core 160 as well as the side panels 126 and 128. In some embodiments, containment flaps 164 and 166 are included in the waist containment structure 142.

Side panels 126 and 128, which may or may not have elastic elements, are ultrasonically bonded and are formed such that the materials of construction provide a manually tearable, non-refastenable region near the seams 127 and 129. The side panels 126 and 128 can incorporate elastic elements which include incorporating a layer of elastic material or an SBL.

The pant structure 112 also desirably includes leg elastics 136 and 138 operatively joined to the crotch area 124. The leg elastics 136 and 138 are positioned along the edges of side panels 126 and 128 and the longitudinal edges 180 and 182 of the pant structure 112 in the crotch area 124. The leg elastics 136 and 138 may assist in holding the pant structure 112, and ultimately the waste containment structure 142 where present, against the body of the wearer or forming seals or gaskets about the legs of the wearer.

Leg elastics 136 and 138 can be stretch bonded to the cover material along the longitudinal edges of the pant structure 112. The waist elastic 143 and 145 elasticizes the front and back waist band regions 120 and 122 of the pant structure 112. Thereafter, each side panel 126 and 128 can be bonded together by seams 127 and 129 so that the pant structure 112 defines the waist opening 134 and the pair of leg openings 130 and 132.

The pant structure 112 and the trunk cover 114 are joined at the waist of the trunk garment 110. The longitudinal ends 135 and 137 of the waist band regions 120 and 122 of the pant structure 112 are joined to the waist regions 131 and 133. Waist elastic members 143 and 145 are position between the longitudinal ends 135 and 137 and the waist regions 131 and 133. The pant structure 112 is desirably attached to the front panel 115 and the back panel 121, but not to the crotch section 149 of the cover 114.

Desirably, the waist elastic members 143 and 145 are made up of at least two spunbond layers with elastic positioned between the spunbond layers. the longitudinal ends 135 and 137, waist regions 131 and 133, and the waist elastic members 143 and 145 are desirably bonded together by adhesives, however other methods of bonding discussed above can be utilized. The waist regions 131 and 133 of the trunk cover 114 may be attached to the pant structure 112 around the entirety of the waist opening 134 or only a portion thereof. The waist elastic members 143 and 145 may be stretch bonded to the cover 114 or bonded in a relaxed state to a gathered portion of the waist regions of the panels of the cover 114. One suitable method was discussed above.

The waist elastic members 143 and 145 may be stretch bonded to the waist regions 120 and 122 of the trunk cover 114 and the waist band regions 120 and 122 of the pant structure 112 or bonded in a relaxed state to a gathered portion of the waist band regions 120 and 122 of the pant structure 112 and the waist regions 131 and 139 of the trunk cover 114. One suitable method for attaching the waist elastics 143 and 145 is disclosed in U.S. Pat. No. 4,639,949 issued Feb. 7, 1987, to Ales et al., which is incorporated herein by reference.

The longitudinal ends 135 and 137 and the waist regions 131 and 133 end at the top edge or near the top edge of the waist elastic members 143 and 145. This allows the longitudinal ends 135 and 137 and the waist regions 131 and 133 to be cut off simultaneously.

To construct the trunk cover 114 of the desired embodiment for trunk garment 110, the front panel section 115 may be joined with the back panel 121 along seams 187 and 189 and at the inseam 147 in the crotch area 149 and to pant structure 112 at the front and the back waist band regions 120 and 122 near the waist opening 134. The term "finished pant" means a three-dimensional pant that can be used for its intended purpose.

The trunk garment 110 may include a waste containment structure 142. (See FIG. 5) The waste containment structure 142 as illustrated includes a backsheet 158, a bodyside liner 156, an absorbent core 160 sandwiched between the backsheet 158 and the bodyside liner 156. The backsheet 158 and bodyside liner 156 are desirably longer and wider than the absorbent core 160, so that the peripheries of the backsheet 158 and liner 156 form margins which may be sealed together using ultrasonic bonds, thermal bonds, adhesives, or other suitable means. The absorbent core 160 may be attached to the backsheet 158 and/or the bodyside liner 156 using ultrasonic bonds, adhesives, or other suitable means.

The waste containment structure 142 may also include additional components to assist in the acquisition, distribution and storage of waste material. For example, the waste containment structure 142 may include a transport layer, discussed above.

The waste containment structure 142 can be constructed by supplying bodyside liner and backsheet materials and sandwiching an individual absorbent core 160 between the backsheet 158 and bodyside liner 156. The side peripheries of the backsheet 158 and bodyside liner 156 outward of the absorbent core 160 can be joined with side panel material and sealed together. Individual waste containment structure 142 can then be cut from the continuous supply of backsheet and bodyside liner materials. The waste containment structure 142 may optionally be T-shaped, I-shaped, hourglass-shaped, or irregularly-shaped.

The description of the backsheet 58 is equally applicable to the description of the backsheet 158. In addition, however, wherein the trunk garment 110 has a trunk cover 114, the backsheet 158 of the waste containment structure 142 can be made with a liquid pervious material, to allow for some breathability of the structure, while the a cover (not shown) is impervious, allowing for fast-drying and containment of any fluid passing through the structure.

The description of the bodyside liner 56 is equally applicable to the description of the bodyside liner 156. See the description above.

As described previously, the side panels 126 and 128 may be formed of a material capable of stretching in one direction or capable of stretching in at least two substantially perpendicular directions. The one-directional stretch material may comprise a composite material including at least one gatherable web bonded to at least one elongated elastic web. The elastic web may be an elastic film or nonwoven fibrous elastic webs such as meltblown elastomeric fibrous webs. In one embodiment, the side panels 126 and 128 comprise a stretch bonded laminate formed of a pre-stretched elastic meltblown inner layer sandwiched between and attached to a pair of spunbond polypropylene nonwoven webs having a basis weight of about 0.4 oz/yd$^2$ (13.6 gsm). For a more complete description, see the discussion above.

Suitable two-directional stretch materials suitable for use in the side panels 126 and 128 were discussed above in the descriptions for side panels 26 and 28. See also the description of the leg elastics 36 and 38, and waist elastic members 43 and 45. The information can be applied to the leg elastics 136 and 138, and waist elastic members 143 and 145.

The trunk cover 114 can be desirably constructed of a single layer comprising film layer, nonwoven layer, or any other suitable liquid permeable or liquid impermeable material, desirably having a cloth-like feel. The trunk cover 114 is constructed of a single spunbonded polypropylene nonwoven web having a basis weight of about 0.5 oz/yd$^2$ (17 gsm) to about 2.0 oz/yd$^2$ (68 gsm). In the case of trunk garment 110, the trunk cover 114 desirably comprises a material having a basis weight of from about 0.5 oz/yd$^2$ (17 gsm) to about 2.0 oz/yd$^2$ (68 gsm), desirably 1.0 oz./yd$^2$ to 2.0 oz./yd$^2$ at least in the crotch and buttocks regions of the trunk cover 114.

The present invention relates to a disposable garment comprising 10 a skirt cover 14 having a front panel 15 having two side edges 17 and 19, and a waist region 31, and an opposing bottom edge 39 between the side edges 17 and 19, and a back panel 21 having two side edges 23 and 25 and a waist region 33 and an opposing bottom edge 41 between the side edges 23 and 25; and, a pant structure 12 having a front waist band region 20 and a back waist band region 22 longitudinally spaced and terminating in longitudinal ends 35 and 37, a crotch area 24 between the front and back waist band regions 20 and 22, and a pair of side panels 26 and 28, the pant structure 12 having a waist opening 34, two leg openings 30 and 32, and waist elastic members 43 and 45, wherein the waist region 31 of the front panel 15 and the waist region 33 of the back panel 21 of the skirt cover 14 are non-refastenably engaged to the front waist band region 20 and the back waist band region 22 having the waist elastic members 43 and 45 positioned between the panels 15 and 21 and the waist band regions 20 and 22.

The disposable garment 10 may further comprise a waste containment structure 42 having a backsheet 58, a bodyside liner 56, and an absorbent core 60. The disposable garment 10 wherein the side panels 26 and 28 of the pant structure 12 include elastic elements. The bottom edges 39 and 41 are hemmed. The skirt cover 14 extends below the crotch area 24 of the pant structure 12. The side edges 17 and 19 of the front panel 15 and the back panel 21 of the skirt cover 14 are joined together to form a one piece skirt cover 14.

Another embodiment of the present invention relates to a disposable garment comprising a skirt cover 14 having a front panel 15 having two side edges 17 and 19 and a waist region 31 and an opposing bottom edge 39 between the side edges 17 and 19 and a back panel 21 having two side edges 23 and 25 and a waist region 33 and an opposing second bottom edge 41 between the side edges 23 and 25; a pant structure 12 having a front waist band region 20 and a back waist band region 22 longitudinally spaced and terminating in longitudinal ends 35 and 37, a crotch area 24 between the front and back waist band regions 20 and 22, and a pair of side panels 26 and 28, the pant structure 12 having a waist opening 34, two leg openings 30 and 32 and waist elastic members 43 and 45; and, a waste containment structure 42 having a backsheet 58, a bodyside liner 56, and an absorbent core 60, wherein the waist region 31 of the front panel 15 and the waist region 33 of the back panel 21 of the skirt cover 14 are non-refastenably engaged to the front waist band region 20 and the back waist band region 22 having the waist elastic members 43 and 45 positioned between the panels 15 and 21 and the waist band regions 20 and 22.

Another embodiment of the present invention relates to a disposable garment 110 comprising a trunk cover 114 having a front panel 115 having two side edges 117 and 119 and a waist region 131 and an opposing bottom edge 139 between the side edges 123 and 125 and a back panel 121 having two side edges 123 and 125 and a waist region 133 and an opposing bottom edge 141 between the side edges 123 and 125, wherein the side edges 117 and 123/119 and 125 are joined to form side seams 187 and 189 and the front panel 115 and the back panel 121 joined together at an inseam 147, defining a crotch section 149 extending centrally between the front and back panels 115 and 121 defining a waist opening 134 and two leg openings 193 and 195 at opposite sides of the crotch section 149; and, waist elastic members 143 and 145, wherein the waist region 131 of the front panel 115 and the waist region 133 of the back panel 121 of the trunk cover 114 are non-refastenably engaged with the waist elastic members 143 and 145.

The present invention further comprising a pant structure 112 having a front waist band region 120 and a back waist band region 122 longitudinally spaced and terminating in longitudinal ends 135 and 137, a crotch area 124 between the front and back waist band regions 120 and 122, and a pair of side panels 126 and 128, the pant structure 112 having a waist opening 134 and two leg openings 130 and 132. The present invention may also include the pant structure non-refastenably engaged to the waist elastics 143 and 145.

Another embodiment of the present invention relates to a disposable garment 110 comprising a trunk cover 114 having a right front panel 151 having two side edges 117 and 159 and a waist region 161 and an opposing bottom edge 163 between the side edges 117 and 159, a left front panel 153 having two side edges 119 and 165 and a waist region 167 and an opposing bottom edge 169 between the side edges 119 and 165, a right back panel 155 having two side edges 123 and 171 and a waist region 173 and an opposing bottom edge 175 between the side edges 123 and 171, and a left back panel 157 having two side edges 125 and 177 and a waist region 179 and an opposing bottom edge 181 between the side edges 125 and 177 wherein the side edges 117 and 123/119 and 125/159 and 165/171 and 177 are joined to form side seams 187 and 189 and center seams 183 and 185, and the front panels 151 and 153 and the back panels 155 and 157 joined together at an inseam 147, defining a crotch section 149 extending centrally between the front and back panels 151, 153, 155, and 157 defining a waist opening 134 and two leg openings 193 and 195 at opposite sides of the crotch section 149; and, waist elastic members 143 and 145, wherein the waist regions 161 and 167 of the front panels 151 and 153 and the waist regions 173 and 179 of the back panels 155 and 157 of the trunk cover 114 are nonrefastenably engaged with the waist elastic members 143 and 145.

The present invention also relates to a disposable garment 110 comprising a trunk cover 114 having a front panel 115 having two side edges 117 and 119 and a waist region 131 and an opposing bottom edge 139 between the side edges 117 and 119 and a back panel 121 having two side edges 123 and 125 and a waist region 133 and an opposing bottom edge 141 between the side edges 119 and 123, wherein the side edges 117 and 123/119 and 125 are joined to form side seams 187 and 189 and the front panel 115 and the back panel 121 joined together at an inseam 147, defining a crotch section 149 extending centrally between the front and back panels 115 and 121 defining a waist opening 184 and two leg openings 186 and 188 at opposite sides of the crotch section 149; a pant structure 112 having a front waist band region 120 and a back waist band region 122 longitudinally spaced and terminating in longitudinal ends 135 and 137, a crotch area 149 between the front and back waist band regions 120 and 122, and a pair of side panels 126 and 128, the pant structure defining a waist opening 134 and two leg openings 130 and 132; and, waist elastic members 143 and 145, wherein the waist region 131 of the front panel 115 and the waist region 133 of the back panel 121 of the trunk cover 114 are non-refastenably engaged to the front waist band region 120 and the back waist band region 122 having the waist elastic members 143 and 145 positioned between the panels 115 and 121 and the waist band regions 120 and 122.

The present invention further comprising a waste containment structure 142 having a backsheet 158, a bodyside liner 156, and an absorbent core 160. The side panels 126 and 128 of the pant structure 112 include elastic elements.

The present invention relates to a disposable garment 110 comprising a trunk cover 114 having a right front panel 153 having two side edges 117 and 159 and a waist region 161 and an opposing bottom edge 163 between the side edges 117 and 159, a left front panel 153 having two side edges 119 and 165 and a waist region 167 and an opposing bottom edge 169 between the side edges 119 and 165, a right back panel 155 having two side edges 123 and 171 and a waist region 173 and an opposing bottom edge 175 between the side edges 123 and 171, and a left back panel 157 having two side edges 125 and 177 and a waist region 179 and an opposing bottom edge 181 between the side edges 123 and 171 wherein the side edges 117 and 123/119 and 125/159 and 165/171 and 177 are joined to form side seams 187 and 189 and center seams 183 and 185, and the front panels 151 and 153 and the back panels 155 and 157 joined together at an inseam 147, defining a crotch section 149 extending centrally between the front and back panels 151, 153, 155, and 157 defining a waist opening 134 and two leg openings 193 and 195 at opposite sides of the crotch section 149; a pant structure 112 having a front waist band region 120 and a back waist band region 122 longitudinally spaced and terminating in longitudinal ends 135 and 137, a crotch area 124 between the front and back waist band regions 120 and 122, and a pair of side panels 126 and 128, the pant structure 112 defining a waist opening 134 and two leg openings 130 and 132; and, waist elastic members 143 and 145, wherein the waist regions 161 and 167 of the front panels 151 and 153 and the waist regions 173 and 179 of the back panels 155 and 157 of the trunk cover 114 are non-refastenably engaged to the front waist band region 120 and the back waist band region 122 having the waist elastic members 143 and 145 positioned between the panels 151, 153, 155, and 157 and the waist band regions 120 and 122.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, only one rather than both ends of the waste containment structure can be elastically connected to the cover. Therefore, the invention should not be limited by the specific embodiments described, but only by the claims.

The materials of which the garment 10 and the trunk garment 110 are made can be any materials specifically desired by the user or manufacturer. Numerous examples of materials used in constructing the garment 10 and the trunk garment 110 are described in the aforementioned U.S. patents and patent applications incorporated by reference herein.

What is claimed is:

1. A disposable garment comprising:

a. a skirt cover having a front panel having two side edges and a waist region and an opposing bottom edge between the side edges and a back panel having two side edges and a waist region and an opposing bottom edge between the side edges; and, b. a pant structure having a front waist band region and a back waist band region longitudinally spaced and terminating in longitudinal ends, a crotch area between the front and back waist band regions, and a pair of side panels wherein the side panels of the pant structure include elastic elements, the pant structure having a waist opening, two leg openings and waist elastic members, wherein the waist region of the front panel and the waist region of the back panel of the skirt cover are non-refastenably engaged to the front waist band region and the back waist band region having the waist elastic members positioned between the panels and the waist band regions.

2. The disposable garment according to claim 1, further comprising a waste containment structure having a backsheet, a bodyside liner, and an absorbent core.

3. The disposable garment according to claim 1, wherein the bottom edges are hemmed.

4. The disposable garment according to claim 1, wherein the skirt cover extends below the crotch area of the pant structure.

5. The disposable garment according to claim 1, wherein the side edges of the front panel and the back panel of the skirt cover are joined together to form a one piece skirt cover.

6. A disposable garment comprising:

a. a skirt cover having a front panel having two side edges and a waist region and an opposing bottom edge between the side edges and a back panel having two side edges and a waist region and an opposing second bottom edge between the side edges;

b. a pant structure having a front waist band region and a back waist band region longitudinally spaced and terminating in longitudinal ends, a crotch area between the front and back waist band regions, and a pair of side panels wherein the side Panels of the pant structure include elastic elements, the pant structure having a waist opening, two leg openings and waist elastic members; and, c. a waste containment structure having a backsheet, a bodyside liner, and an absorbent core, wherein the waist region of the front panel and the waist region of the back panel of the skirt cover are non-refastenably engaged to the front waist band region and the back waist band region having the waist elastic members positioned between the panels and the waist band regions.

* * * * *